(12) United States Patent
Walls et al.

(10) Patent No.: US 9,791,431 B2
(45) Date of Patent: Oct. 17, 2017

(54) CUTTINGS-BASED WELL LOGGING

(71) Applicant: Ingrain, Inc., Houston, TX (US)

(72) Inventors: Joel Walls, Houston, TX (US);
Elizabeth Diaz, Houston, TX (US);
Sonia Jam, Houston, TX (US); Bryan Guzman, Houston, TX (US)

(73) Assignee: Ingrain, Inc., Houston, TX (US)

( * ) Notice: Subject to any disclaimer, the term of this patent is extended or adjusted under 35 U.S.C. 154(b) by 724 days.

(21) Appl. No.: 14/335,817

(22) Filed: Jul. 18, 2014

(65) Prior Publication Data

US 2015/0025863 A1    Jan. 22, 2015

Related U.S. Application Data

(60) Provisional application No. 61/856,521, filed on Jul. 19, 2013.

(51) Int. Cl.
*G06F 7/60* (2006.01)
*G06F 17/10* (2006.01)
*G01N 33/24* (2006.01)

(52) U.S. Cl.
CPC .................................. *G01N 33/241* (2013.01)

(58) Field of Classification Search
CPC .................................................... G01N 33/241
USPC ............................................................. 703/2
See application file for complete search history.

(56) References Cited

U.S. PATENT DOCUMENTS

| | | | | |
|---|---|---|---|---|
| 4,947,682 A | * | 8/1990 | Anderson | E21B 47/065 374/10 |
| 7,569,810 B1 | * | 8/2009 | Troxler | G01N 33/42 250/269.1 |
| 8,081,796 B2 | * | 12/2011 | Derzhi | E21B 49/005 378/53 |
| 8,081,802 B2 | * | 12/2011 | Dvorkin | G01N 23/046 175/249 |
| 2003/0070480 A1 | * | 4/2003 | Herron | G01V 11/00 73/152.14 |

* cited by examiner

*Primary Examiner* — Timothy A Mudrick
(74) *Attorney, Agent, or Firm* — Chamberlain Hrdlicka

(57) ABSTRACT

Methods and systems for cuttings-based well logging, including a method that includes converting measurements of cuttings samples from one or more depth intervals of a wellbore to a concentration percent of one or more elements, determining a one or more minerals of the cuttings samples from the concentration percent and building a mineralogy model for the cuttings sample based at least in part on a gravimetric conversion of the concentration percent of at least some of the one or more elements to a concentration percent of the one or more minerals. The method further includes normalizing the concentration percent of the one or more minerals, computing a photo-electric absorption factor (PEF) of the cuttings samples for each of the one or more depth intervals, and presenting to a user a log of the computed PEF as a function of wellbore depth.

12 Claims, 5 Drawing Sheets

CUTTINGS-BASED WELL LOGGING

CROSS-REFERENCE TO RELATED APPLICATION

This application claims priority to Provisional U.S. Application Ser. No. 61/856,521, titled "Cuttings-Based Well Logging Methods" and filed Jul. 19, 2013 by Joel Walls, Elizabeth Diaz, Sonia Jam and Bryan Guzman, which is incorporated herein by reference.

BACKGROUND

Oilfield operators drill wellbores to access subterranean reservoirs. Often they desire to characterize the formations that are penetrated by the wellbores. For example, such characterization facilitates estimation of the amount and accessibility of hydrocarbons in reservoir rocks. However, it can be difficult to perform such characterization, particularly when it is infeasible to insert appropriate tools in the wellbore and/or to obtain core samples.

It would be desirable to characterize the penetrated formations based on the cuttings obtained from the drilling process itself. Such a process preferably would overcome certain obstacles, e.g., the cuttings are necessarily much smaller than core samples, only statistically associated with given wellbore intervals, and subject to contamination by the drilling fluid used to flush them from the wellbore.

BRIEF DESCRIPTION OF THE DRAWINGS

A better understanding of the various disclosed embodiments can be obtained when the following detailed description is considered in conjunction with the attached drawings, in which.

It should be understood that the drawings and corresponding detailed description do not limit the disclosure, but on the contrary, they provide the foundation for understanding all modifications, equivalents, and alternatives falling within the scope of the appended claims.

DETAILED DESCRIPTION

The paragraphs that follow describe illustrative methods and systems for performing cuttings-based well logging. Illustrative drilling environments are first described, followed by a description of sieving of rock fragments or "cuttings" into a sample of a desired size fraction used for analysis. The preparation of the cuttings sample is then described, followed by an the description of several methods that processes and combine measurements of the sample to compute a photoelectric effect index (PEF) value that is used to characterize the rock for the depth interval from which the sample originated. The disclosed methods are also presented within the context of an illustrative system and a software-based implementation by said system. Together, the system and software may perform at least part of the disclosed methods to characterize the depth interval of interest.

Figure 1:
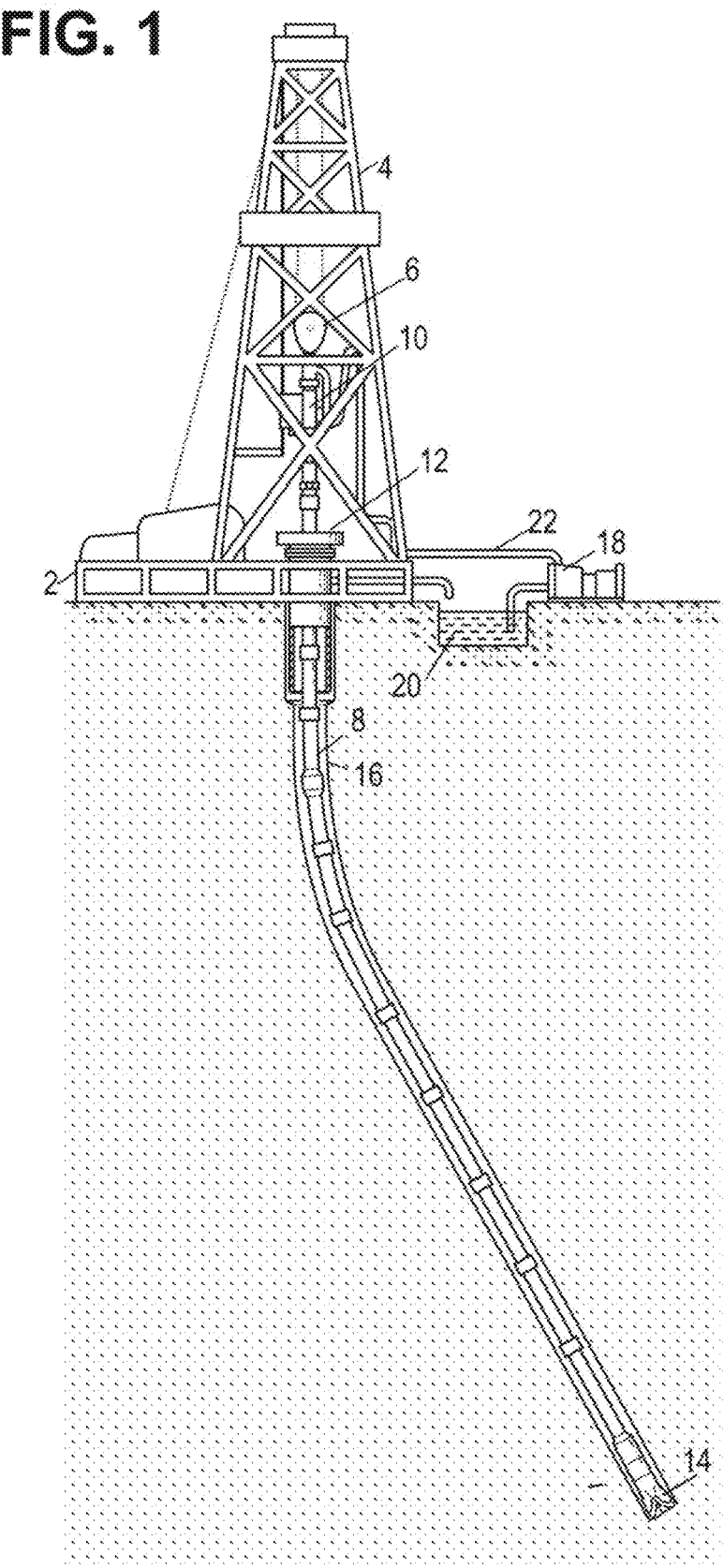
FIG. 1 is a schematic diagram of an illustrative drilling environment.

The disclosed methods and systems are best understood in the context of the larger systems in which they operate. Accordingly, FIG. 1 shows an illustrative drilling environment. A drilling platform 2 supports a derrick 4 having a traveling block 6 for raising and lowering a drill string 8. A top drive 10 supports and rotates the drill string 8 as it is lowered through the wellhead 12. A drill bit 14 is driven by a downhole motor and/or rotation of the drill string 8. As bit 14 rotates, it creates a wellbore 16 that passes through various formation layers. A pump 18 circulates drilling fluid 20 through a feed pipe 22, through the interior of the drill string 8 to drill bit 14. The fluid exits through orifices in the drill bit 14 and flows upward through the annulus around the drill string 8 to transport cuttings to the surface. At the surface, the drilling fluid is filtered to remove the cuttings and the drilling fluid is recirculated back down the drill string 8 to repeat the process.

The cuttings filtered out from the drilling fluid are representative of the rock formation depth interval from which they originate from. The disclosed methods identify one or more cuttings that best represent the depth interval of the thousands of cuttings transported to the surface. The disclosed methods provide a cost-effective way to investigate and characterize a formation that provides a valid representation of the intervals of interest.

Figure 2:
FIG. 2 is an image of an illustrative sample splitter.

In at least some illustrative embodiments, the cuttings are delivered to a lab still mixed with the drilling fluid, which is removed from the cuttings so that they can be analyzed more accurately. Once they have been cleaned, the cuttings from the interval are sieved into a specific size fraction (within a tolerance range, e.g., 1 mm-3 mm) so as to analyze a similar group of cuttings, reflecting the drilling conditions of the depth interval from which the cuttings originated. Unbiased selection and collection of a sieved, clean cuttings sample is achieved using a sample splitter for unbiased splitting (e.g. Gilson Universal Stainless Steel Mini-Splitter; many other splitters are known in the art and are not discussed further), such as splitter 200 shown in FIG. 2. In other illustrative embodiments, additional divisions may be produced so that other cuttings analysis can be performed in addition to the analysis described below.

Once collected, the cuttings sample may be employed to determine the PEF of the formation penetrated by the wellbore as a function depth. The PEF is a measurement of the absorption of low-energy gamma rays by the formation in barns per electron. Because the PEF is a function of the aggregate atomic number of the elements within the formation, it operates as an indicator of the formation's mineralogy. PEF logs thus can be used to identify "sweet spots" along a wellbore where the mineralogy indicates a higher probability of locating hydrocarbons or other natural resources. The PEF can be derived from X-ray fluorescence (XRF) measurements of the cuttings, though other measurement techniques such as X-ray diffraction (XRD), multi-energy X-ray computed tomography (CT), Fourier transform infrared spectroscopy (FTIR), laser-induced breakdown spectroscopy (LIBS), Raman spectroscopy and/or any other type of electromagnetic spectroscopy may also be used, and all such measurement techniques are within the scope of the present disclosure.

Figure 3:
FIG. 3 is an image of an illustrative handheld micro X-ray fluorescence device.

In at least some illustrative embodiments, the cuttings sample is pulverized so that it can be prepared into a pressed pellet that is subjected to a bulk analysis, e.g., XRF analysis using a handheld micro-XRF device such as XRF device 300 shown in FIG. 3, though other non-handheld devices may also be used. In XRF analysis a sample is exposed to short-wavelength X-rays, ionizing the sample's atoms. This ionization results from the ejection of one or more inner orbital electrons of the atoms. This creates instability in the atom and electrons in higher orbitals drop down into the lower orbitals, releasing energy in the form of a photon. This absorption and subsequent re-emission of radiation in this manner is referred to as fluorescence. The XRF device analyzes the fluorescent radiation by sorting the energies of the photons (energy-dispersive analysis) and/or by separating the wavelengths of the radiation (wavelength-dispersive analysis). The concentration of a sample can be determined from this analysis because the intensity of each element's characteristic radiation is directly related to the amount of that element in the sample.

For illustrative embodiments utilizing XRF analysis, the division sample is pulverized and placed into a sample die and then covered with a binding powder (e.g., boric acid, cellulose, etc.). The die is placed under a press that compresses the sample using significant pressure (e.g., 20 tons of pressure), yielding a uniform pellet. In other illustrative embodiments, fused beads or pellets may also or instead be produced. The resulting pellet is analyzed using, for example, XRF 300 of FIG. 3 to determine the sample's elemental concentration. The XRF device 300 is pointed at the sample and activated to expose the sample to radiation and measure the resulting re-emissions. The result is displayed on the device as shown, and may also be transferred to a computing system for further processing as discussed in more detail below. Results from the elemental analysis of this pellet are now considered representative of the rock concentration throughout the sample interval and are referred to as the bulk analysis results.

After measurements are performed on the sample, the measurements are processed and converted into a concentration percent such as weight percent or volume percent. For the illustrative XRF embodiment presented, the XRF counts are processed using an appropriate calibration so that the counts can be converted into elemental weight percent. An example of such a calibration is described in Rowe, Loucks, Ruppel, and Rimmer, "Mississippian Barnett Formation, Ft Worth Basin, Tex.: Bulk Geochemical Inferences and Mo-TOC Constraints on the Severity of Hydrographic Restriction", Chemical Geology 257 (2008) 16-25. Certain elements may be emphasized more than others based on expected formation properties.

To compute a weight percent of the minerals based on the weight percent of the major elements of a sample, a gravimetric conversion may be used that takes into account the concentration of minerals. In at least some illustrative embodiments, a conversion model is generated that is based on a concentration of rock minerals specified for each formation. Similar approaches have been discussed in published literature (e.g., Brumsack H., "Geochemistry of recent TOC-rich sediments from the Gulf of California and the Black Sea" Geologische Rundschau 78/3 (1989) 851-882), which are used to compute the oxides compounds for major elements. Other approaches use one or more tests that measure the total inorganic content to provide the conversion from elements to minerals (e.g., Algeo T. J., Hannigan R., Rowe H., Brookfield M., Baud A., Krystyn L., and Ellwood B. B., "Sequencing events across the Permian-Triassic boundary, Guryul Ravine (Kashmir, India)" Paleoecology 252 (2007) 328-346).

In at least some illustrative embodiments, the generated conversion model utilizes elemental percentages to compute mineral percentages that in turn are normalized to add up to one hundred percent. Based on the normalized mineral percentage, cuttings for a specific depth interval are characterized in terms of three groups of minerals (e.g., carbonate, silica, and clay). The PEF value for each depth interval is computed using a linear relation between the cuttings mineral concentrations and the PEF values for each group of minerals, as described in more detail below.

The mineralogy determined by the conversion model for a given formation may differ from previously generated models or models, which is the result of differences in the model constants. To account and adjust for such discrepancies, in at least some illustrative embodiments the conversion model for a given formation is validated against XRD measurements performed on a limited number of cuttings depth intervals. The resulting XRD counts are calibrated and processed, producing a mineral weight percent. The accuracy of the conversion model is improved by adjusting the model constants to reduce the error between the computed mineralogy (e.g., computed based upon XRF measurements) and the XRD-based mineralogy measurements.

In other illustrative embodiments, FTIR measurement and analysis techniques are used in addition to or alternatively to determine the mineralogy and/or the total organic carbon (TOC) of the sample. Either transmission or reflectance FTIR techniques, including but not limited to, e.g., diffused reflectance Fourier transform infrared spectroscopy (DRIFTS) and attenuated total reflectance Fourier transform infrared spectroscopy (ATR), may be used to determine mineralogy and/or the PEF values. The measurements and the results of the analysis are presented to a user for the various depth intervals corresponding to the cuttings samples. As with the PEF data, the FTIR and TOC data may both be presented as logs to a user.

In still other illustrative embodiments, bulk density values and logs are derived from the cuttings samples. Using, for example, the same quantity of cuttings as employed for the XRF analysis, the bulk density is measured using any of a number of techniques, including but not limited to multi-energy X-ray CT, Archimedes method, gas expansion (Boyles law) and Pycnometers. In alternative embodiments, the quantity of cuttings may be optimized to minimize measurement errors. The quantity of cuttings that are suitable for each density measurement technique depends at least in part on variations in the quality of cuttings samples (e.g., as measured by softness, porosity, etc.) and in the physical condition of the cuttings (e.g., thickness, spherical index, etc.). The derived bulk density measurement values for the various cuttings samples depth intervals may also be presented to a user in the form of a well log.

In at least some illustrative embodiments a cuttings sample depth interval is selected from a group of samples that are associated with a given rock facies. The selected interval is representative of the facies and is selected based at least in part on PEF and bulk density values associated with facies containing hydrocarbons. The selection of the interval may also be based on the mineralogy derived from XRF, XRD and/or FTIR measurements, as well as based upon elemental concentration determinations derived from XRF measurements and/or TOC computations derived from FTIR. Other suitable techniques for the selection of a subsample that characterizes an entire rock or that is representative of rock facies containing hydrocarbons are described in U.S. patent application Ser. No. 13/850,543 by Walls, hereby incorporated in its entirety by reference, and all such techniques are within the scope of the present disclosure.

The PEF and bulk density (ρB) determined as described above can be used to create a cross plot of the two values that identifies areas of interest to geologist and/or petroleum engineers. Such areas are characterized by the presence of organic material, such as kerogen, and by sufficient porosity to support the presence and extraction of resources of interest such as, for example, oil and natural gas. In at least some illustrative embodiments, the cross plots are generated for the cuttings samples and the plot of the data pairs are divided into regions (e.g., 2×2, 3×3, 4×4, etc.). Regions with values for PEF and ρB that are lower relative to those in other regions are generally considered likely to be formations with higher porosity (φ) and organic matter. The selection of depth intervals may thus be based at least in part upon PEF and bulk density, and can optionally be refined further by also taking into account facies studies.

The determination of facies can be achieved using a number of known techniques, for example, by determining facies cubes based upon geologic interpretation as described in U.S. Pat. No. 7,079,953 by Thorne, et al, and/or using a lithofacies classification as described in U.S. Pat. No. 8,126,647 by Hruska, et al. Many other techniques for determining facies will become apparent to those of ordinary skill in the art, and all such techniques are within the scope of the present disclosure.

Once selected as described above, the depth interval(s) may further be characterized in terms of its mineralogy and/or elemental concentration. In at least some illustrative embodiments, such characterization(s) may be performed on the cuttings (rock fragments) as described in PCT App. No. PCT/US2014/046311 by Walls, et al., which is hereby incorporated in its entirety by reference.

Several factors may be taken into account in determining where and how to evaluate reservoir quality and to stimulate production from a gas or oil reservoir (e.g., a shale reservoir). Among these factors are, (a) the brittleness of the formation, which assists with assessing the difficulty in creating a hydraulically connected fracture network during hydro-fracturing operations; (b) the porosity of the formation, which is indicative of the formation's hydrocarbon storage capacity; (c) the organic material content; and (d) the permeability of the formation, which is a primary production-driving parameter. Brittleness is directly related to the mineralogy. For example, the higher the carbonate and quartz content, the more brittle the rock. Conversely, the higher the clay or organic matter content, the less brittle (i.e., more ductile) the formation rock is. The porosity affects the bulk density. The smaller the density of the formation rock, the higher its porosity. Finally, the permeability is often a function of porosity and the grain size of the formation rock, and thus can be assessed from these two characteristics. Techniques for estimating formation brittleness, porosity, organic material content and permeability from multi-energy X-ray CT are described in U.S. patent application Ser. No. 13/738,106 by Dvorkin, hereby incorporate in its entirety by reference. As previously noted, both the PEF and bulk density may also be determined using a multi-energy X-ray CT scan technique.

Thus, three sets of values are derived using the above-described workflow: bulk density, elemental concentration and PEF. Logs for each of these may be combined with other rapid scan data, such as core gamma ray (GR) and/or spectral gamma ray (SGR) data, adding another dimension to the analysis of reservoir quality. In at least some illustrative embodiments, GR- and/or SGR-based estimates of the total clay content or specific clay and other mineral types are included in the mineral balance equation. The inclusion of the GR/SGR data enables additional estimations of the mineral concentration, including the estimation of at least three minerals (e.g., calcite, quartz and illite). In at least some illustrative embodiments, by using SGR to provide a detailed mineral count the computed PEF data can be resolved for more than three mineral constituents, thus providing a more detailed mineralogy assessment and improved brittleness estimates over existing estimation techniques. The improved assessment may also improve the precision of bulk density-to-porosity and kerogen content transforms and more accurate permeability estimates. This is because different mineralogies (particularly clay) imply different grain size, which is one of the principal parameters used in a porosity-to-permeability transform. In at least some illustrative embodiments, one or more of the above-described formation characteristics are presented to the user in the form of a well log.

In at least some illustrative embodiments, the quality of a reservoir is determined by combining the brittleness index, porosity and permeability of formation cuttings samples. The quality is considered high for samples where the three parameters have relatively higher values than other samples, and low where the three parameters have lower values. These three values, together with the relationships between them and the computed mineralogy (XRF-based) and measured bulk density, are used to repopulate existing well logs for the various depth intervals of previously studied wells.

Figure 4:
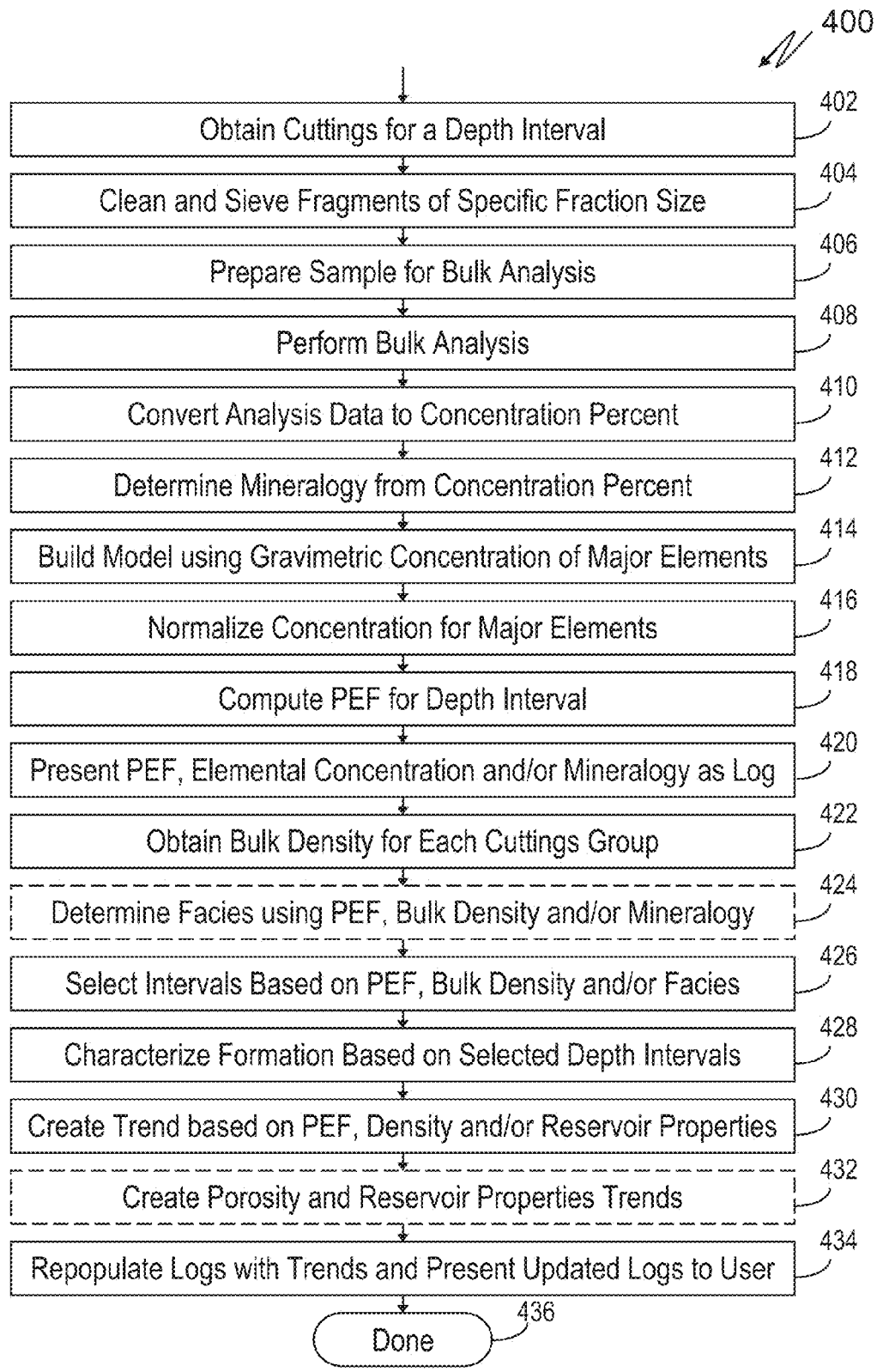
FIG. 4 is a flowchart showing an illustrative method for cuttings-based well logging.
Figure 5:
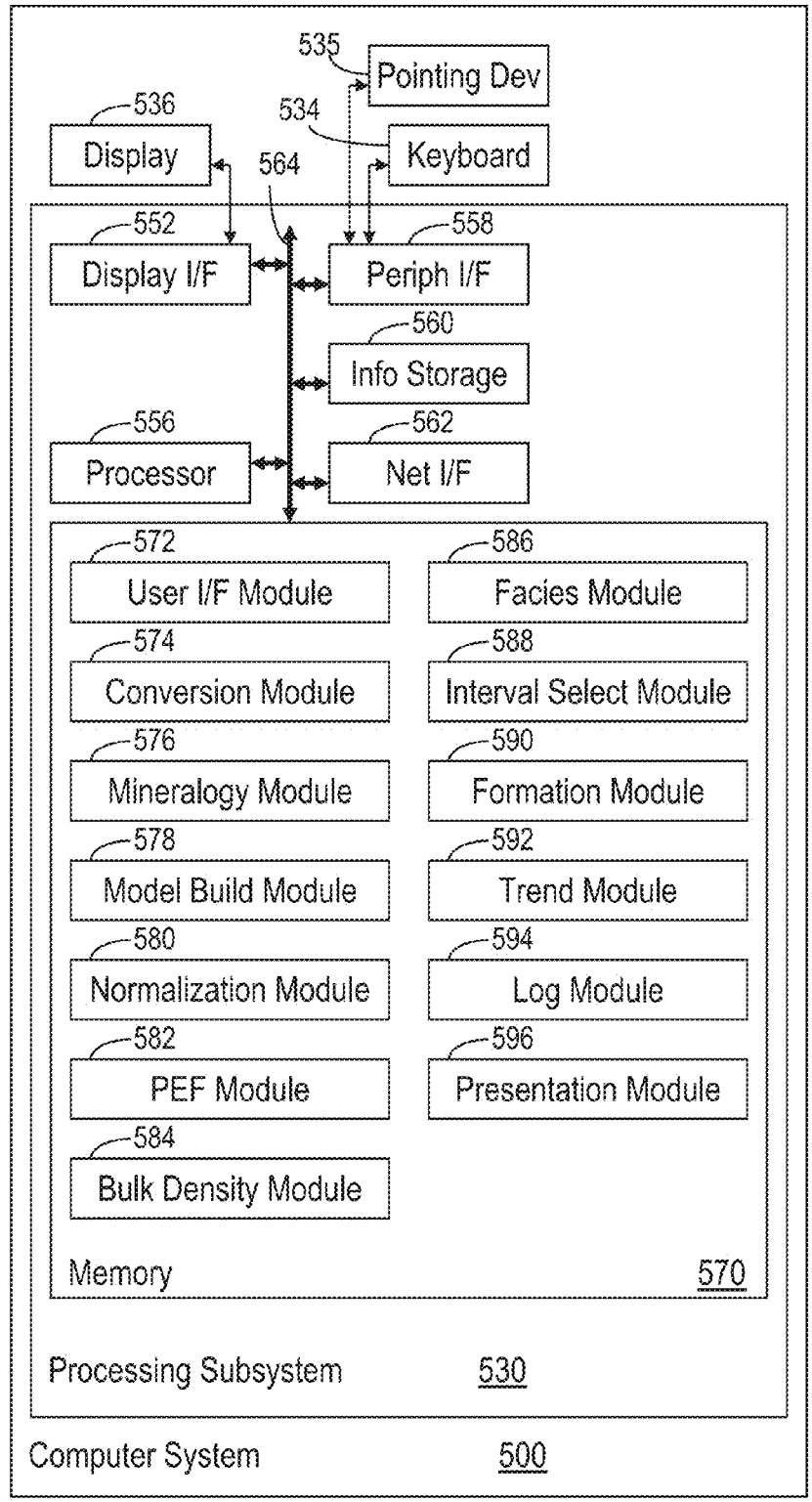
FIG. 5 is a block diagram of a computer system suitable for implementing at least part of the disclosed methods in software.
Figure 6:
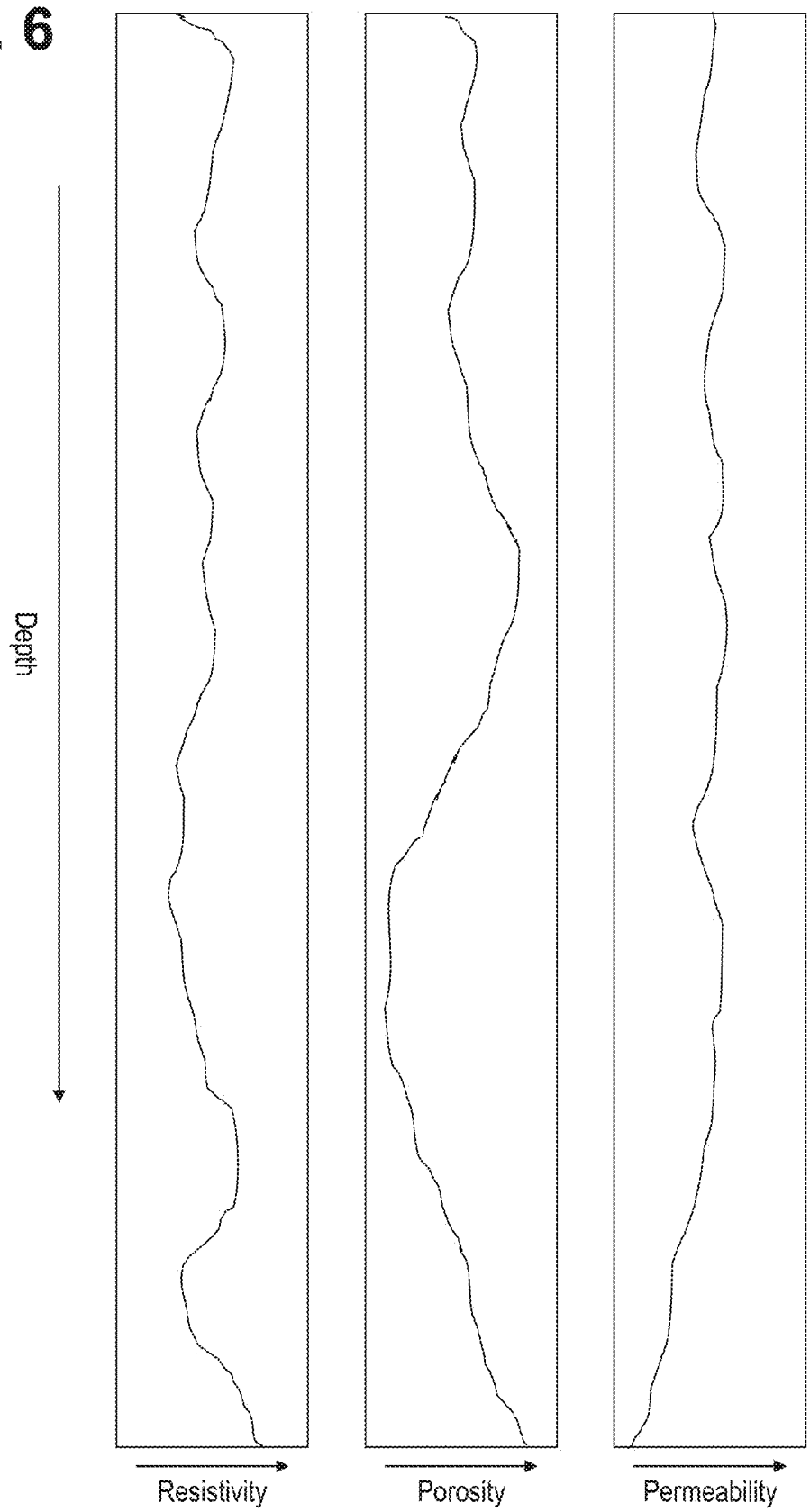
FIG. 6 shows an example of several illustrative well logs of properties of the wellbore.

FIG. 4 shows an illustrative flowchart for the above-described method, while FIG. 5 shows a block diagram of a computer system 5. Both hardware and software components of computer system 500 are shown, which in at least some illustrative embodiments implement at least part of the wellbore depth interval characterization shown as method 400 in FIG. 4 (described in detail below). A user may interact with computer system 500 via keyboard 534, pointing device 535 (e.g., a mouse) and display 536 to configure, control and monitor the execution of the wellbore depth interval characterization.

Located within processing subsystem 530 of computer system 500 is a display interface 552, a processor 556, a peripheral interface 558, an information storage device 560, a network interface 562 and a memory 570. Bus 564 couples each of these elements to each other and transports their communications. Network interface 562 enables communications with other systems (e.g., via the Internet with a central database server housing well logging data). In accordance with user input received via peripheral interface 558 and program instructions from memory 570 and/or information storage device 560, processor 556 processes input from the user and applies it to the well logging data to perform the disclosed methods and present the results to the user. Storage device 560 may be implemented using any number of known non-transitory information storage media, including but not limited to magnetic disks, solid-state storage devices and optical storage disks.

Various software modules are shown loaded into memory 570 of FIG. 5, where they are each accessed by processor 556 for execution. These modules include: User Interface Module 572, which interacts with the input/output devices utilized by the user to interact with processing system 530; conversion module 574, which calibrates and analyzes the data for the cuttings samples to determine a concentration percent; mineralogy module 576, which determines the mineralogy from the concentration percent; model build module 578 which builds a model based on conversion of major elements to corresponding minerals; normalization module 580, which performs the normalization computations; PEF module 582, which computes the PEF values for each depth interval; bulk density module 584 which processes measured bulk density measurements; facies module 586, which determines facies within the formation; interval selection module 588, which selects depth intervals for further processing based on PEF, bulk density and/or facies; formation module 590, which characterizes the formation based upon the selected depth intervals; trend module 592, which generates cross-plots or trends of properties that characterize the formation; log module 594, which generates logs for the various measured and computed values and/or repopulates existing logs; and presentation module 596, which present to a user the results of method 500. In at least some illustrative embodiments, the results are presented in graphical form (e.g., as an image of the various bed layers of a formation within a wellbore depth range), while in other illustrative embodiments the results are presented as well logs.

Referring now to both FIGS. 4 and 5, illustrative method 400 begins by obtaining cuttings for a given depth interval from the drilling fluid expelled during drilling of a wellbore (block 402). The drilling fluid is removed from the cuttings, which are then sieved to produce an unbiased sample of a specific fraction size (block 404) using a sample splitter as previously described. The sample pulverized and formed into a pellet to prepare it for bulk analysis (block 406), and bulk analysis is performed on the pressed pellet (block 408). In at least some illustrative embodiments, the collected analysis data is processed by a computer system such as computer system 500 of FIG. 5. The bulk analysis data is converted into concentration percent, e.g., a weight percent using a calibration technique as previously described (block 410; Conversion Module 574). The resulting concentration percent values are subsequently used to determine mineralogy for each group of cuttings corresponding to each depth interval (block 412; Mineralogy Module 576).

In at least some illustrative embodiments, a mineralogy model is built (block 414; Model Build Module 578) that is based on gravimetric conversions of the major elements of the concentration percent to corresponding minerals. The following equations are examples of such a conversion for three mineral groups, though the equations can specify either a mineral group or a specific mineral:

$$\% \, W_{Carbonate} = \% \, w_n / A \quad (1)$$

$$\% \, W_{Clay} = \% \, w_{n+1} / B \quad (2)$$

$$\% \, W_{Quartz} = \frac{\% \, w_{n+2} - D * \left(\frac{\% \, w_{n+1}}{100}\right)}{C} \quad (3)$$

where:
% $w_i$=weight percent for a selected element i, for i=n, n+1 or n+2,
% $W_j$=weight percent for mineral or mineral group j, for j=Carbonate, Clay or Quartz, and
A, B, C and D=gravimetric conversion constants.

The resulting mineral weight percentages for the major elements are normalized so as to add up to 100% (block 416; Normalization Module 580). Although only three equations corresponding to three mineral groups are shown, more than three equations may be used corresponding to a different number of mineral groups or selected minerals, and all such combinations of equations, minerals and mineral groups are within the scope of the present disclosure.

The PEF of the cuttings associated with a given depth interval is computed based on a linear relation between the normalized weight percentage and the corresponding PEF value for pure minerals (block 418; PEF module 582). In at least some illustrative embodiments, the PEF value is computed as, $$PEF = PEF_n *\% \, NW_n + PEF_{n+1} *\% \, NW_{n+1} + PEF_{n+2} *\% \, NW_{n+2} \quad (4)$$

where:
% $W_j$=weight percent for mineral or mineral group j, for j=Carbonate, Clay or Quartz, and
$PEF_j$=PEF value corresponding to mineral or mineral group j, for j=Carbonate, Clay or Quartz.

The resulting PEF for each depth interval, as well as the corresponding elemental and/or mineralogy is presented to a user, e.g., as a well log (block 420; Presentation Module 594).

In at least some illustrative embodiments, the bulk density for each group of cuttings corresponding to a depth interval is obtained (block 422; Bulk Density Module 584), either by measuring the density of the cuttings as previously described or referencing other sources of density measurement data (e.g., existing wireline log data obtained for the wellbore). Optionally, facies are determined based on the previously determined PEF, bulk density and/or mineralogy (block 424; Facies Module 586. Sub-groups of depth intervals are then selected based upon the PEF, bulk density and/or facies (block 426; Interval Select Module 588), and the formation penetrated by the wellbore is characterized based upon these selected depth intervals (block 428; Formation Module 590). Such a characterization includes a determination of properties such as porosity, TOC and permeability, just to name a few examples.

The PEF and bulk density values as well as the properties characterizing the formation may be used to create trends (block 430; Trend Module 592), which are cross plots of the values/properties that operate to identify inter-relationships between such values and/or properties and to determine statistical correlations. Optionally, additional trends may be generated of porosity and characterization properties (block 432; Trend Module 592). The data from the trends is used to repopulate existing logs (block 434; Log Module 594), which are presented to the user (block 434; Presentation Module 596), ending the method (block 436). It should be noted that although the relationships and properties derived from the trend data are specific to the selected interval(s), in at least some illustrative embodiments the analysis is extended to other depth intervals.

The disclosed methods and systems provide data describing properties that characterize formation rock based on cuttings produced during drilling operations in an economical and efficient manner. They also facilitate the selection of suitable depth intervals associated with such cuttings for further study of reservoir quality and basic rock properties. The determination of bulk density and PEF values and presentation of such values as continuous well logs for the cuttings provide a basis for computing TOC and brittleness logs, which as previously described are useful for identifying formations that are likely to hold useful resources such as oil and natural gas. These and other properties of the formation rock can also be used to assist with determination and validation of the best depth to drill horizontally (target zone) for a vertical or pilot well and, for horizontal wells, to confirm containment within a target zone before making completion decisions. The disclosed methods and systems can provide such information for wells where LWD or wireline data is not available, and can provide additional data points for determining reserve estimations (e.g., when utilizing SEM data). Given the increased use of horizontal wellbores, multilateral wells and coiled tubing, as well as the overall increase in drilling costs in general, which all contribute to a decrease in the availability of rock samples from whole cores, drilled side-wall plugs and other direct data sources, cuttings-based logging is emerging as a valuable and cost-effective source of formation data.

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A method for cuttings-based well logging, the method comprising:
   converting measurements of cuttings samples from one or more depth intervals of a wellbore to a concentration percent of one or more elements;
   determining a one or more minerals of the cuttings samples from the concentration percent;
   building a mineralogy model for the cuttings sample based at least in part on a gravimetric conversion of the concentration percent of at least some of the one or more elements to a concentration percent of the one or more minerals;
   normalizing the concentration percent of the one or more minerals;
   computing a photo-electric absorption factor (PEF) of the cuttings samples for each of the one or more depth intervals; and
   presenting to a user a log of the computed PEF as a function of wellbore depth.

2. The method of claim 1, wherein the one or more depth intervals are presented to a user as part of a graphical representation of formation bed layers traversed by the wellbore or as part of a well log of one or more of the properties of the wellbore.

3. The method of claim 1, wherein the measurements performed are selected from a group of measurement techniques consisting X-ray florescence (XRF), X-ray diffraction (XRD), Fourier transform infrared spectroscopy (FTIR), laser-induced breakdown spectroscopy (LIBS), Raman spectroscopy and electromagnetic spectroscopy.

4. The method of claim 1, wherein the concentration percent comprises a weight percent comprising an elemental weight percent, a mineralogical weight percent or total organic carbon (TOC).

5. The method of claim 1, further comprising:
   determining one or more facies based at least in part on the PEF, a bulk density or the one or more minerals of the cuttings samples for each of the one or more depth intervals or on the one or more minerals;
   selecting at least one depth interval of the one or more depth intervals based at least in part on the PEF for each of the one or more depth intervals or on the one or more facies;
   characterizing one or more properties of the wellbore based upon the at least one depth interval;
   creating one or more trends based on the PEF, the bulk density or porosity of the cutting samples for each of the at least one depth interval or on the one or more facies; and
   repopulating an existing log of the wellbore based upon the one or more trends and presenting the repopulated log to the user.

6. The method of claim 5, wherein the bulk density comprises a measured bulk density of the cutting samples for each of the at least one depth interval or a bulk density measurement corresponding to each of the at least one depth interval and obtained from an existing log of the wellbore.

7. A cuttings-based well logging system, comprising:
   a memory having cuttings-based well logging software; and
   one or more processors coupled to the memory, the software causing the one or more processors to:
      convert measurements of cuttings samples from one or more depth intervals of a wellbore to a concentration percent of one or more elements;
      determine a one or more minerals of the cuttings samples from the concentration percent;
      build a mineralogy model for the cuttings sample based at least in part on a gravimetric conversion of the concentration percent of at least some of the one or more elements to a concentration percent of the one or more minerals;
      normalize the concentration percent of the one or more minerals;
      compute a photo-electric absorption factor (PEF) of the cuttings samples for each of the one or more depth intervals; and
      present to a user a log of the computed PEF as a function of wellbore depth.

8. The system of claim 7, wherein the one or more depth intervals are presented to a user as part of a graphical representation of formation bed layers traversed by the wellbore or as part of a well log of one or more of the properties of the wellbore.

9. The system of claim 7, wherein the measurements performed are selected from a group of measurement techniques consisting X-ray florescence (XRF), X-ray diffraction (XRD), Fourier transform infrared spectroscopy (FTIR), laser-induced breakdown spectroscopy (LIBS), Raman spectroscopy and electromagnetic spectroscopy.

10. The system of claim 7, wherein the concentration percent comprises a weight percent comprising an elemental weight percent, a mineralogical weight percent or total organic carbon (TOC).

11. The system of claim 7, wherein the software further causes the one or more processors to:
   determine one or more facies based at least in part on the PEF, a bulk density or the one or more minerals of the cuttings samples for each of the one or more depth intervals or on the one or more minerals;
   select at least one depth interval of the one or more depth intervals based at least in part on the PEF for each of the one or more depth intervals or on the one or more facies;
   characterize one or more properties of the wellbore based upon the at least one depth interval;
   create one or more trends based on the PEF, the bulk density or porosity of the cutting samples for each of the at least one depth interval or on the one or more facies; and
   repopulate an existing log of the wellbore based upon the one or more trends and presenting the repopulated log to the user.

12. The system of claim 11, wherein the bulk density comprises a measured bulk density of the cutting samples for each of the at least one depth interval or a bulk density measurement corresponding to each of the at least one depth interval and obtained from an existing log of the wellbore.

* * * * *